United States Patent [19]

Shimomura et al.

[11] Patent Number: 5,061,976
[45] Date of Patent: Oct. 29, 1991

[54] FET ELECTRODE WITH CARBON GATE

[75] Inventors: Takeshi Shimomura; Shuichiro Yamaguchi; Takanao Suzuki, all of Fuji; Noboru Oyama, Fuchu, all of Japan

[73] Assignee: Terumo Kabushiki Kaisha, Tokyo, Japan

[21] Appl. No.: 687,214

[22] PCT Filed: Nov. 19, 1987

[86] PCT No.: PCT/JP87/00900
§ 371 Date: Jul. 19, 1989
§ 102(e) Date: Jul. 19, 1989

[87] PCT Pub. No.: WO88/04049
PCT Pub. Date: Jun. 2, 1988

Related U.S. Application Data

[63] Continuation of Ser. No. 362,392, Jul. 19, 1989, abandoned.

[30] Foreign Application Priority Data

Nov. 20, 1986 [JP] Japan ............................ 61-275250

[51] Int. Cl.$^5$ ............................ H01L 29/66
[52] U.S. Cl. .................... 357/25; 357/23.15; 357/8; 204/418; 204/416
[58] Field of Search ............. 357/23.15, 25, 23.7, 357/8; 204/418, 416

[56] References Cited

U.S. PATENT DOCUMENTS

| | | | |
|---|---|---|---|
| 3,598,713 | 8/1971 | Baum et al. | 204/195 |
| 3,926,764 | 12/1975 | Ruzicka et al. | 204/195 |
| 3,932,233 | 1/1976 | Ruzicka et al. | 204/195 |
| 3,957,612 | 5/1976 | Niedrach et al. | 204/195 |
| 3,957,613 | 5/1976 | Macur | 204/195 |

(List continued on next page.)

FOREIGN PATENT DOCUMENTS

| | | |
|---|---|---|
| 0186210 | 7/1986 | European Pat. Off. . |
| 3134760A | 9/1982 | Fed. Rep. of Germany . |
| 52-30490 | 8/1977 | Japan . |
| 57-63444 | 4/1982 | Japan . |
| 57-118153 | 7/1982 | Japan . |
| 58-167951 | 10/1983 | Japan . |
| 59-164952 | 9/1984 | Japan . |
| 59-17662 | 10/1984 | Japan . |
| 59-176662 | 10/1984 | Japan . |
| 60-52759 | 3/1985 | Japan . |
| 60-73351 | 4/1985 | Japan . |
| WO85/04480 | 10/1985 | PCT Int'l Appl. . |
| 89314 | 8/1979 | U.S.S.R. . |

OTHER PUBLICATIONS

Oyama et al., "Ion Selective Microelectrode Prepared by Modifying an Electrode with Polymers", International Electroanalytical Symposium, May 27–29, 1987, Schaumberg, Ill., pp. 122–124.

Oyama et al., "A New Type of Ion-Selective Microelectrodes Using Electropolymerized Thin Films", The Electrochemical Society Symposium, Honolulu, Hawaii, Oct. 18–23, 1987, pp. 1–2.

Esashi et al., "Biomedical Cation Sensor Using Field Effect of Semiconductor", Proceedings of the 6th Conference on Solid State Devices, Tokyo, 1974, Supplement to the Journal of the Japan Society of Applied Physics, vol. 44, 1975, pp. 339–343.

(List continued on next page.)

Primary Examiner—William Mintel
Attorney, Agent, or Firm—Burns, Doane, Swecker & Mathis

[57] ABSTRACT

The surface of a gate insulating membrane of an ion-selective field-effect transistor (ISFET) (10) is coated with a carbon thin membrane (4), and the surface of the latter is coated with an electrolytic polmerization membrane (3) of 2,6 xylenol. The ISFET obtained exhibits hydrogen-ion selectivity, little drift, high stability and little response to light. If the surface of the electrolytic polmerization membrane (3) of 2,6 xylenol is coated with another ion-selective membrane or enzyme-active membrane, various ions and the concentration of a biological substrate can be measured.

11 Claims, 3 Drawing Sheets

U.S. PATENT DOCUMENTS

| | | | |
|---|---|---|---|
| 4,052,285 | 10/1977 | Dobson | 204/195 |
| 4,115,209 | 9/1978 | Fraiser et al. | 204/1 T |
| 4,198,851 | 4/1980 | Janata | 73/23 |
| 4,214,968 | 7/1980 | Battaglia et al. | 204/195 |
| 4,280,889 | 7/1981 | Szonntagh | 204/195 |
| 4,282,079 | 8/1981 | Chang et al. | 204/195 |
| 4,305,802 | 12/1981 | Koshiishi | 204/195 |
| 4,454,007 | 6/1984 | Pace | 204/1 T |
| 4,512,870 | 4/1985 | Kohara et al. | 357/25 X |
| 4,549,951 | 10/1985 | Knudson et al. | 204/416 |
| 4,561,962 | 12/1985 | Kankare et al. | 204/415 |
| 4,563,263 | 1/1986 | Oyama et al. | 204/418 |
| 4,615,954 | 10/1986 | Solomon et al. | 429/27 |
| 4,632,732 | 12/1986 | Fog et al. | 204/1 T |
| 4,753,719 | 6/1988 | Yamaguchi et al. | 204/418 |
| 4,798,664 | 1/1989 | Yamaguchi et al. | 204/418 |
| 4,816,118 | 3/1989 | Oyama et al. | 357/25 X |
| 4,839,020 | 6/1989 | Yamaguchi et al. | 204/431 |
| 4,861,454 | 8/1989 | Ushizawa et al. | 204/414 |
| 4,981,570 | 1/1991 | Yamaguchi et al. | 357/25 X |
| 5,001,531 | 3/1991 | Yamaguchi | 357/25 |

OTHER PUBLICATIONS

Patent Abstracts of Japan, vol. 9, No. 122, May 28, 1985, Japanese Kokai No. 60-7357.

Patent Abstracts of Japan, vol. 8, No. 159, Jul. 24, 1984, Japanese Kokai No. 59-57156 (Apr. 2, 1984).

Oyama et al., "Electrochemical Properties of Electropolymerized Poly (1-Pyrinamin) Films", Bull. Chem. Soc., Japan 59-2071-2080 (1986).

Ma et al., "Organic Analysis Using Ion-Sensitive Electrodes", Academic Press, 1982, pp. 62 and 70.

Ryan, "Electrochemical Detectors Fundamental Aspects and Analytical Application" Plenum Press, (Apr. 26, 1985), p. 7.

Ammann, "Ion Selective Microelectrodes", Springer-Verlang, N.Y., pp. 5-7.

Tamura et al., "Coated Wire Sodium- and Potassium--Electrodes Based on Bis(Crown Ether) Compounds", Analytical Chem., vol. 54, No. 7, Jun. 1982, p. 1224.

Wuthier et al., "Tin Organic Compounds as Neutral Carriers for Anion Selective Electrodes"Analytical Chemistry, vol. 56, No. 3, Mar. 1984, pp. 535-538.

Norov et al., "Calcium-Selective Electrode Without an Internal Reference Soluting", Journal of Analytical Chemistry, vol. 34, No. 8, Part 1, Aug. 1979, pp. 1139-1162.

Oyama et al., "Hydrogen Ion Selective Microelectrode Prepared by Modifying an Electrode with Polymers", Analytical Chemistry 1987, vol. 59, pp. 258-262, Jan. 1987.

Oyama et al., "Ion Selective Electrode Prep. by Mod. an Electrode with Polymers", Tokyo Seminar on Macromolecular Complexes, Tokyo Univ., Oct. 14, 1987.

Snell et al., "Surface Modified Electrodes", Chem. Soc. Rev., 1979, 8, 259-282.

Faulkner, "Chemical Microstructures on Electrodes", Chem. Eng. News, 1984, 27, pp. 28-45.

FET ELECTRODE WITH CARBON GATE

This application is a continuation of application Ser. NO. 07/362,392, filed July 19, 1989 now abandoned.

TECHNICAL FIELD

This invention relates to a FET electrode and, more particularly, to an ion-sensitive FET electrode.

BACKGROUND ART

FET electrodes, long known in the art, utilize the principle of a field-effect transistor (FET). With regard to the structure and operation of a FET electrode, an impurity is diffused in a p-type substrate, which comprises a substrate of a metal oxide/semiconductor insulative membrane (p-type $SiO_2/Si_3N_4$), on the gate portion thereof, thereby forming an n-type source and a drain electrode. When a positive voltage is applied to the electrode at the gate portion, the potential of the p-type semiconductor in the vicinity of a redox membrane drops to induce electrons within the p-type semiconductor. A layer of these electrons forms a channel along which electrons flow from the source to the drain to produce a drain current. The amount of this drain current is controlled by the gate voltage. Since the voltage at the gate is proportional to the $H^+$ ion activity, the FET electrode can be used as a pH-MOSFET However, a FET electrode of this type responds to light, besides exhibiting a large amount of drift and poor stability.

DISCLOSURE OF THE INVENTION

An object of the present invention is to solve the foregoing problems of the prior art and provide a FET electrode exhibiting little drift, high stability and little response to light.

As means for solving the foregoing problems, the FET electrode of the present invention comprises a FET, a carbon thin membrane coating a gate insulator of the FET, and an organic thin membrane coating the carbon thin membrane.

In the arrangement of the invention, the FET measures the concentration of $H^+$ ion based on a potential, which corresponds to the activity of the $H^+$ ion, produced on the gate portion by the organic thin membrane. Meanwhile, the carbon thin membrane reduces drift, stabilizes the adhesion between the gate insulator of the FET and the organic thin membrane and shuts out light.

Thus, in accordance with the invention, there is provided a FET electrode exhibiting little drift, high stability and little response to light.

Moreover, since the membrane covering the gate produces a potential which corresponds to the $H^+$ ion, there can be provided a FET electrode which operates on the principle of the field effect, namely a FET electrode having the following structural arrangement, which is characteristic of the field effect:

(1) An amplifier having an high input impedance is unnecessary.
(2) Since a negative feedback circuit is constructed by utilizing the amplifying action of the device, the output resistance of the electrode can be kept to a low several thousand kilohms and electrical disturbances can be reduced.

BEST MODE FOR CARRYING OUT THE INVENTION

Figure 1:
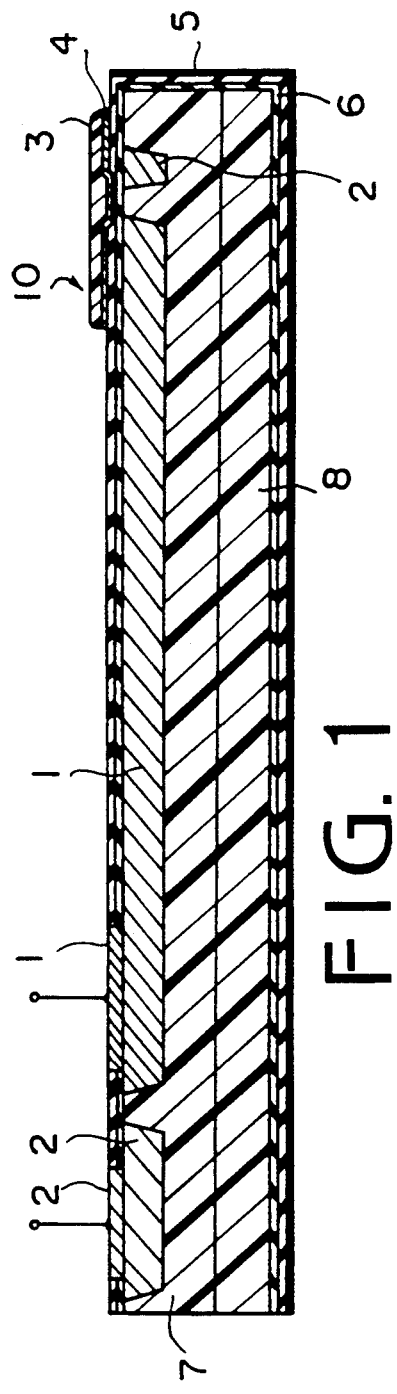
FIG. 1 is a sectional view illustrating an integrated-type FET electrode of the present embodiment.

First, examples of forming a carbon thin membrane will be illustrated.

Formation Example 1

By using carbon (high-purity graphite carbon G161AS, manufactured by Tokai Carbon K.K.) as a target, a carbon thin membrane was deposited on the surface of sapphire (on silicon) by a sputtering process.

The conditions for sputtering were 100 W, $8 \times 10^{-2}$ Torr, 20 hrs, a substrate temperature of less than 150° C. and an argon atmosphere.

As a result, there was obtained a carbon-coated sapphire substrate having a carbon thin membrane thickness of about 1.0 $\mu$m.

Formation Example 2

The sputtering conditions were the same as those in Experiment 1 except for the fact that a methane gas atmosphere was used.

As a result, there was obtained a carbon-coated sapphire substrate having a carbon thin membrane thickness of about 1.2 $\mu$m. A strong membrane could be produced, and the specific resistance was $1 \times 10^{-3} \Omega$cm.

Formation Example 3

The sputtering conditions were the same as those in Formation Example 1 except for the fact that a hydrogen gas atmosphere was used.

As a result, there was obtained a carbon-coated sapphire substrate having a carbon thin membrane thickness of about 0.8 $\mu$m. The specific resistance was $1 \times 10^{-3} \Omega$cm.

Comparison Formation Example

As in Formation Example 1, carbon was used as the target to coat the surface of sapphire (on silicon) with a carbon thin membrane by a sputtering process.

The conditions for sputtering were 600 W, $1 \times 10^{-2}$ Torr, 20 min, a substrate temperature of 300° C. and an argon atmosphere.

As a result, there was obtained a carbon-coated sapphire substrate having a carbon thin membrane thickness of about 1000 Å.

An electrode and a FET electrode using the formed carbon-coated sapphire substrate will now be described.

EXAMPLE 1

The specific resistance of the carbon-coated sapphire substrate (1 cm $\times$ 1 cm in size) obtained in Formation Example 1 was about $10^{-3} \Omega$cm. The periphery of the substrate was insulated with a silicone resin (KE348W, manufactured by Shinetsu Silicone K.K.). A silver coaxial line (0.6 mm$\phi$ in size) was attached to one side by means of an electrically conductive adhesive to form a lead wire. The resulting electrode (active electrode) had a response area of about 0.5 mm×0.5 mm at its tip.

The surface of the electrode was coated with a polymeric membrane of 2,6 xylenol by an electrolytic polymerization process carried out under the following conditions:
Composition of electrolyte solution
0.5M 2,6 xylenol
0.2M NaClO
acetonitrile solution (solvent)

ELECTROLYTIC POLYMERIZATION CONDITIONS

The electrolyzing potential was swept three times (sweep rate: 50 mV/sec) from 0 to +1.5V (vs. SSCE), followed by carrying out constant-potential electrolysis for 10 min at a constant potential of +1.5V.

Experiment 1

Using the redox membrane-coated carbon-sapphire electrode fabricated in Example 1, the relationship between the electromotive force produced across this electrode and a reference electrode (an Ag/AgCl electrode) and a change in pH in a phosphate buffer solution was determined. As a result, a linear relationship was found over a wide pH range of pH 1.0–9.0, and the slope of the straight line was 58–59 mV/pH (25° C.), thus substantially approximating the Nernst theoretical equation.

The speed of response was substantially the same as that of a redox membrane-coated carbon electrode (coated wire-type electrode), namely 5–30 sec (pH range of pH 5 –9).

Thus, a semiconductor substrate (silicon or sapphire) could be coated with a stable carbon thin membrane.

EXAMPLES 2 AND 3

Redox membrane-coated, carbon-membrane silicon substrate electrodes were fabricated under the same conditions as set forth in Example 1.

Experiments 2 and 3

A change in pH with respect to the emf developed by the electrodes prepared in Examples 2 and 3 was measured as in Experiment 1. As a result, a linear relationship was found over a wide pH range of pH 1.0–9.0, and the slope of the straight line was 58 mV/pH (25° C.), thus substantially approximating the Nernst theoretical equation. The speed of response was a quick 5–30 sec.

Example 4

Figure 2:
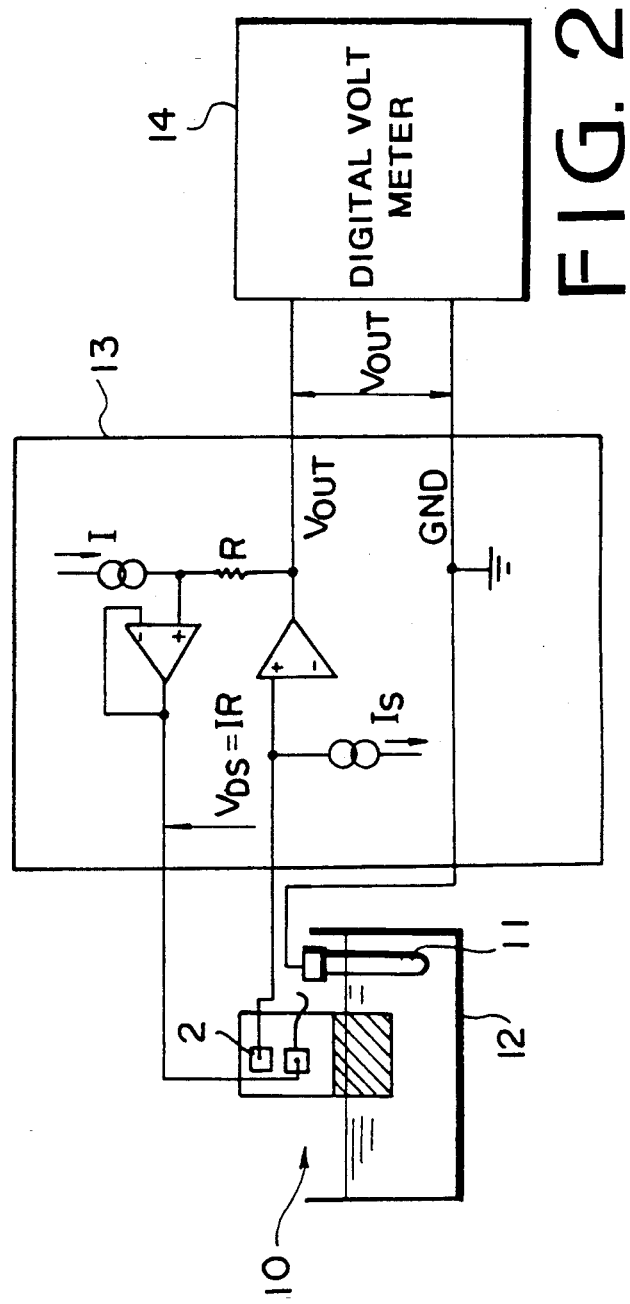
FIG. 2 is a view for describing an apparatus for measuring the FET electrode of the present embodiment.

As shown in FIG. 1, a FET electrode 10 was prepared by coating the gate insulator of a MOSFET with a carbon thin membrane, and coating the latter with a polymeric membrane of 2,6 xylenol (set forth in Example 1) as an organic thin membrane by means of an electrolytic polymerization process. Numeral 1 denotes a drain, 2 a source, 3 the polymeric membrane of 2,6 xylenol, 4 the carbon thin membrane, 5 a silicon nitride membrane, 6 a silicon oxide membrane, 7 p-type silicon, and 8 sapphire The emf developed by the FET electrode 10 thus prepared was measured with respect to the pH of a liquid specimen 12 using the measurement apparatus shown in FIG. 2. Numeral 11 denotes a reference electrode, 13 a measurement circuit, and 14 a digital voltmeter. Measurement was performed under the following conditions: $I_s = 100$ μA, $V_{DS} = 4$V, temperature = 25° C.

Figure 3:
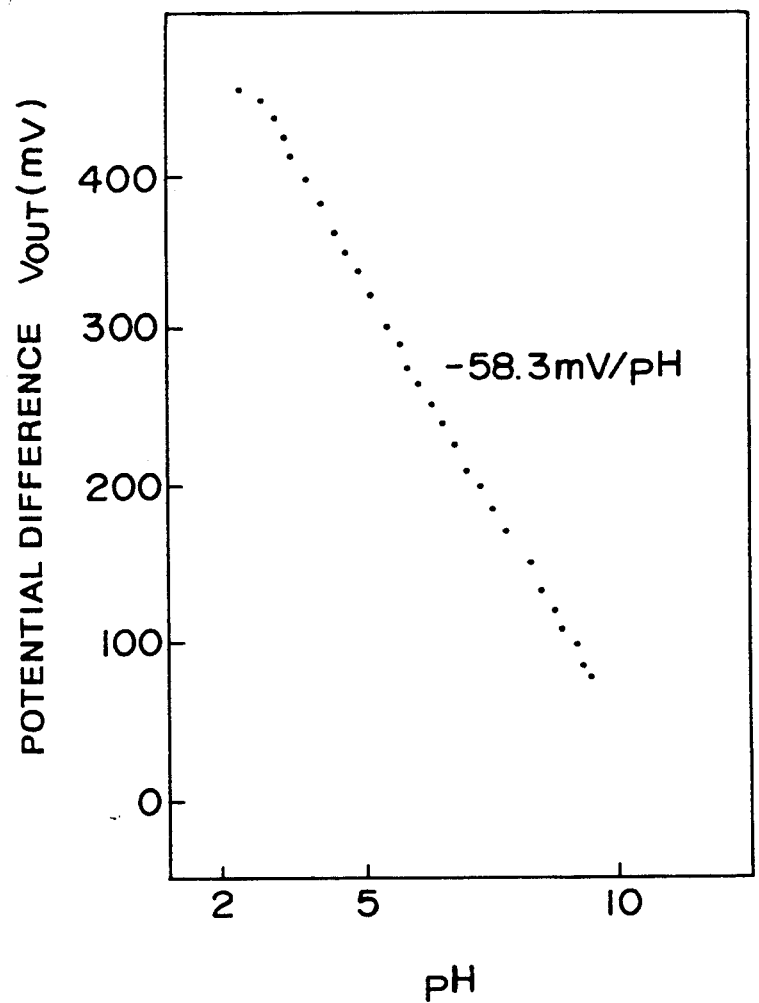
FIG. 3 is a view illustrating the results obtained by measuring the FET electrode of the present embodiment.

As indicated by the results shown in FIG. 3, the slope of $V_{OUT}$/pH (= −58.3 mV/pH) is a straight line. This well approximates the Nernst theoretical equation. The speed of response obtained was 5–30 sec. The MOSFET characteristics ($I_D$-$V_{GS}$ and $I_D$-$V_{DS}$) of the FET sensors where the characteristics peculiar to the respective FET's.

Figure 4:
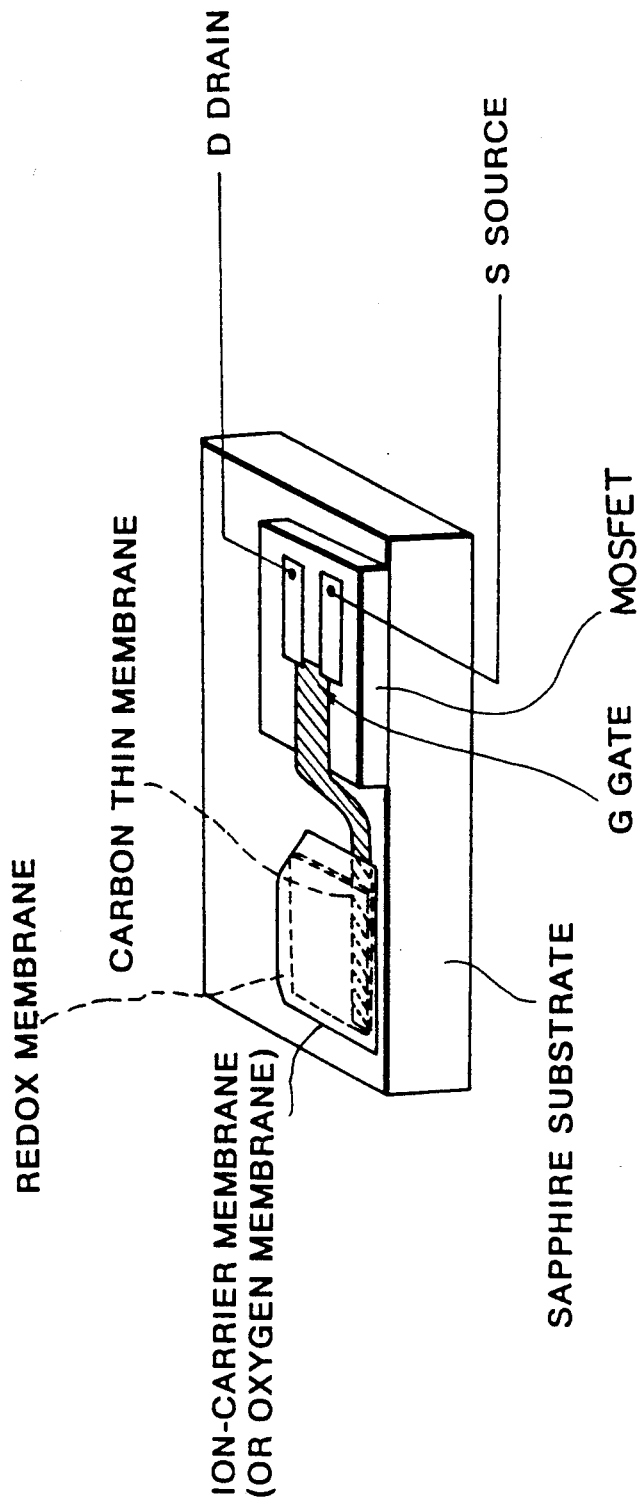
FIG. 4 is a perspective view of an isolated-type FET electrode.

Though the present embodiment has been described with regard to the integrated-type FET electrode shown in FIG. 1, the same results can be obtained even with an isolated gate-type FET electrode of the kind shown in FIG. 4. The same results can also be obtained using a p-type silicon substrate or an n-type silicon substrate as the substrate. Preferably, the specific resistance of the carbon-coated sapphire substrate is less than 10 Ωcm, particularly less than 1 Ωcm and, most preferred over all, less than $1 \times 10^{-3}$ Ωcm, as illustrated in the present embodiment.

The FET electrode can be used as a biosensor, such as an ion-selective FET sensor, a gas sensor for oxygen or the like and an enzyme sensor, by coating the the organic thin membrane of the FET electrode of the present embodiment with an ion-carrier membrane (a neutral carrier membrane), an oxygen-active membrane or an enzyme-fixed membrane, etc.

What is claimed is:

1. A FET device comprising:
   a FET having a source, a drain, a channel for linking between the source and the drain and a gate for controlling current flow in the channel by field effect,
   an insulator over said channel of said FET, a carbon membrane coating said insulator and forming said gate, and
   an organic membrane formed on a surface of said carbon membrane by an electrolytic oxidative polymerization process.

2. The FET device according to claim 1, wherein said carbon membrane possesses, in part, a multi-surfaced structure, and the specific resistance is less than 10 Ωcm following application of the carbon membrane.

3. The FET device according to claim 1, wherein said organic membrane is a membrane which manifests an oxidation-reduction response.

4. The FET device according to claim 1, further comprising and ion-carrier membrane coating said organic membrane.

5. The FET device according to claim 1, further comprising an oxygen-active membrane coating said organic membrane.

6. The FET device according to claim 1, wherein said carbon membrane is further extended from said FET, and said organic membrane is formed on a surface of said extended carbon membrane.

7. A FET device comprising
   a FET having a source, a drain, a channel for linking between the source and the drain and a gate for controlling current flow in the channel by field effect, one of the source and the drain surrounding the other;
   an insulator over said channel of said FET;
   a carbon membrane coating a portion of said insulator far from both electrodes of the source and the drain and forming said gate; and
   an organic membrane formed on a surface of said carbon membrane by an electrolytic oxidative polymerization process.

8. The FET device of claim 7, wherein said carbon membrane possesses, in part, a multi-surfaces structure, and the specific resistance is less than 10 $\Omega$cm following application of the carbon membrane.

9. The FET device of claim 7, wherein said organic membrane is a membrane which manifests an oxidation-reduction response.

10. The FET device of claim 7, further comprising an ion-carrier membrane coating said organic membrane.

11. The FET device of claim 7, further comprising an oxygen-active membrane coating said organic membrane.

* * * * *